United States Patent [19]
Dee et al.

[11] Patent Number: 5,379,724
[45] Date of Patent: Jan. 10, 1995

[54] ULTRASOUND TEAT DIP

[75] Inventors: Alejandro Dee, Roselle; Charles Gradle, Berwyn, both of Ill.

[73] Assignee: Babson Bros. Co., Naperville, Ill.

[21] Appl. No.: 96,028

[22] Filed: Jul. 22, 1993

[51] Int. Cl.$^6$ .................... A01K 29/00; A61D 11/00
[52] U.S. Cl. .................................................. 119/158
[58] Field of Search .................. 119/14.01, 14.08, 156, 119/157, 158, 159; 128/24 AA, 328, 660.03; 433/119; 604/22

[56] References Cited

U.S. PATENT DOCUMENTS

| | | | |
|---|---|---|---|
| 2,970,073 | 1/1961 | Prange | 128/24 AA |
| 3,828,776 | 8/1974 | Sparr, Sr. | 119/158 X |
| 4,073,289 | 2/1978 | Fahim | 128/24 AA |
| 4,077,401 | 3/1978 | Fahim | 128/24 AA |
| 4,078,556 | 3/1978 | Fahim | 128/24 AA |
| 4,282,880 | 8/1981 | Gardineer et al. | 128/660 |
| 4,787,394 | 11/1988 | Ogura | 128/660.03 |
| 4,942,868 | 7/1990 | Vago | 128/24 AA |
| 4,970,992 | 11/1990 | Aiken | 128/158 |
| 5,048,520 | 9/1991 | Vago | 128/24 AA |
| 5,178,134 | 1/1993 | Vago | 128/24 AA |

Primary Examiner—Gene Mancene
Assistant Examiner—Thomas Price
Attorney, Agent, or Firm—Wood, Phillips, VanSanten, Hoffman & Ertel

[57] ABSTRACT

An ultrasound teat dip comprises a dip cup having a well adapted to receive a supply of a germicide and an upper opening for receiving a teat to be dipped in the germicide, in use. A sonic transducer is operatively coupled to the well to sonically vibrate the well to produce cavitation in the germicide supply. A storage vessel defines a reservoir for storing a supply of germicide. The storage vessel is secured to the dip cup. A flow tube transfers germicide stored in the reservoir to the well to refill the dip cup with germicide.

11 Claims, 1 Drawing Sheet

ULTRASOUND TEAT DIP

FIELD OF THE INVENTION

This invention relates to a teat dip and, more particularly, to a teat dip incorporating ultrasound technology.

BACKGROUND OF THE INVENTION

Mastitis is caused by an infection of the udder of dairy cows, where the mammary gland becomes inflamed. Mastitis adversely affects the quantity and quality of milk produced in infected cows. The infection itself can also result in permanent injury or death of the animal. Though prevalent since the time of domestication, the advent of high volume, automatic milking systems has contributed to an increase of mastitis occurrences.

To control the numbers of mastitis causing microorganisms, and thereby reduce the chances of infection, disinfection regimens have been employed. One such regimen entails dipping or spraying the cow's teats with a chemical germicide before and after milking. These germicides, which are known as teat dips and teat sprays, are designed to kill those organisms known to cause mastitis. Though effective, they have been unable to prevent significant numbers of mastitis cases from developing on some farms using these products. This may be due in pan to improper hygiene practices and inadequately functioning milking equipment.

One reason that mastitis occurrences are still significant relates to the unique conditions the chemical germicides have to work under. While generally effective under ideal conditions, the efficacy of germicidal agents can be comprised by various extraneous factors. On dairy farms, teats, especially the ends where the teat orifice or canal is located, can be damaged or scarred from heavy use. In addition, teats tend to be wrinkled, especially after milking when they are no longer filled with milk. These conditions produce areas or crevices which can harbor microorganisms. Upon exposure to teat dipping or spraying, these areas can remain sequestered from the killing effects of the germicide. Further, teats can contain a heavy amount of residual milk or dirt on their surface before dipping. This increased "organic load" can further inhibit the germicidal efficacy of teat dips or sprays.

The present invention is intended to provide an apparatus and method that allows for better penetration by teat dips to those sequestered areas harboring bacteria.

SUMMARY OF THE INVENTION

In accordance with the invention there is provided a teat dip incorporating use of ultrasound technology.

Broadly, them is disclosed herein an ultrasound teat dip comprising a dip cup having a well adapted to receive a supply of a germicide and an upper opening for receiving a teat to be dipped in the germicide, in use. A sonic transducer is operatively coupled to the well to sonically vibrate the well to produce cavitation in the germicide supply. Means are provided for connecting the ultrasonic transducers to an electrical supply to drive the transducer.

It is a feature of the invention that the transducer comprises an ultrasonic transducer operatively coupled to the well to vibrate the well at an ultrasonic frequency.

In accordance with another aspect of the invention there is disclosed an ultrasound teat dip comprising a dip cup having a well adapted to receive a supply of a germicide and an upper opening for receiving a teat to be dipped in the germicide, in use. A sonic transducer is operatively coupled to the well to sonically vibrate the well to produce cavitation in the germicide supply. A storage vessel defines a reservoir for storing a supply of germicide. Means operatively secure the storage vessel to the dip cup. Means are provided for transferring germicide stored in the reservoir to the well to refill the dip cup with germicide. Finally, means are provided for connecting the ultrasonic transducer to an electrical supply to drive the transducer.

It is a feature of the invention that the storage vessel comprises a jar having a top defining an upper opening and the securing means comprises a cap integrally formed with the dip cup for receiving the jar top.

It is another feature of the invention that the transferring means comprises a tube extending between the reservoir and the receptacle.

It is still another feature of the invention that the reservoir is formed of a pliable material which can be squeezed to force germicide through the tube to the receptacle.

In accordance with another aspect of the invention, there is disclosed a method of performing a pre-milking or post-milking teat dip operation comprising the steps of filling a dip cup having an upper opening with a supply of germicide, sonically vibrating the dip cup to transmit sound waves through the germicide supply contained therein, and positioning the dip cup in proximity to a cow's udder to receive a teat in the germicide supply for a select period of time.

It is a feature of the invention that the positioning step comprises maintaining the teat dipped in the germicide for a time period in the range of one to fifteen seconds.

Further features and advantages of the invention will be readily apparent from the specification and from the drawing.

DETAILED DESCRIPTION OF THE INVENTION

Figure 1:
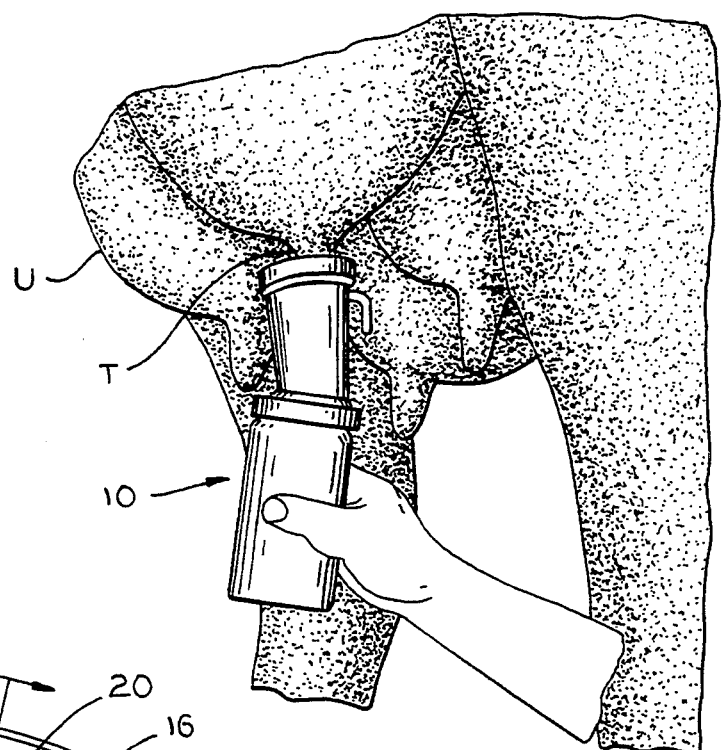
FIG. 1 is a perspective view illustrating a method in accordance with the invention for performing a teat dip operation.

Referring to FIG. 1, a teat dip 10 is shown for performing a pre-milking or post-milking dip operation on the udder U of a dairy cow. Particularly, a cow's teat T is dipped in the teat dip 10, as described below.

Figure 2:
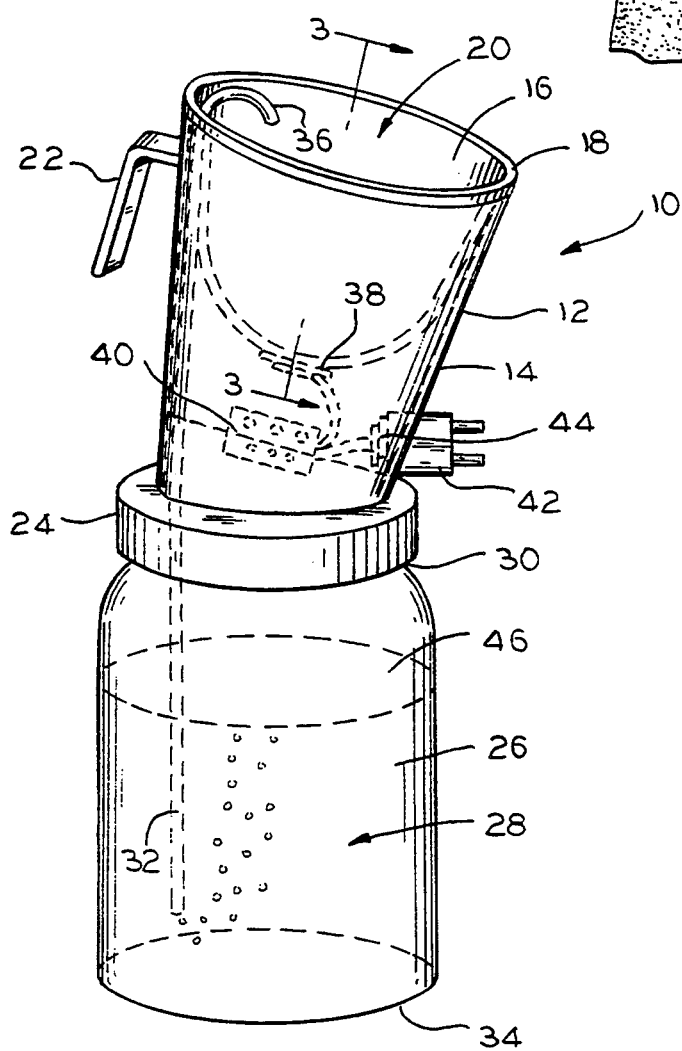
FIG. 2 is an elevation view of the dip cup used in the method of FIG. 1.
Figure 3:
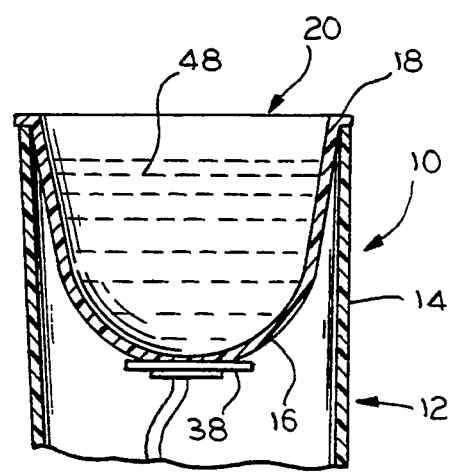
FIG. 3 is a sectional view taken along the line 3—3 of FIG. 2.

Referring also to FIGS. 2 and 3, the teat dip 10 includes a dip cup 12. The dip cup 12 is integrally formed of pliable plastic construction including an outer, generally cylindrical wall 14 receiving an upwardly opening cup-shaped well 16. The well 16 and wall 14 are connected at an upper flange 18 defining an upper opening 20. The flange 18 is adapted to receive a cap (not shown). An integrally formed handle 22 is connected at one side of the side wall 14.

Formed at the bottom of the side wall 14 is a circular coupling element or flange 24. The flange 24 receives a vessel 26. The vessel 26 is also formed of pliable plastic construction in the shape of a typical jar defining an internal reservoir 28. The vessel 26 narrows upwardly to a neck 30 securable to the flange 24 by any known means, such as a threaded connection. A fill tube 32 extends from a position proximate a bottom wall 34 of the vessel 26 and upwardly into the dip cup 12 to an outlet end 36 disposed within the well 16.

An ultrasonic transducer 38 is operatively secured to the dip cup well 16, see FIG. 3. The transducer 38 converts alternating current energy above 20 KHz to mechanical vibrations of the same frequency to produce acoustic waves. The transducer 38 is connected to a conventional drive 40 connected via a plug 42 to a conventional AC supply. A switch 44 is disposed between the plug 42 and the drive 40 for selectively connecting power to operate the transducer 38.

In use, the storage vessel reservoir 28 is filled with a supply 46 of a liquid germicide. The germicide supply 46 may be of any known type for performing a teat dip operation. Prior to performing the teat dip operation, the vessel 26 is squeezed to force germicide from the reservoir 28, up the tube 32 into the well 16 so that a supply 48 of germicide is received therein, see FIG. 3. The plug 42 being connected to an electrical supply and the switch 44 being in an "on" position causes the well 16 to be vibrated at an ultrasonic frequency. This vibration causes sound waves to be transmitted through the dip cup supply 48 to cause cavitation. This is due to the production of alternating high and low pressures in the liquid supply 48. During the low pressure stage, millions of bubbles form and grow, producing cavitation or formation of cavities. At high pressure, the bubbles collapse or implode, releasing enormous amounts of energy. The energy is released instantaneously in all directions to penetrate every surface and invade all recesses and openings. The teat dip 10 is then positioned proximate the cow udder U to receive a teat T in the germicide supply 48 for a select period of time, see FIG. 1. The operation of the ultrasonic transducer 38 provides more effective germicidal penetration into the cracks and crevices frequently present on the cow's teats.

The dip time period is sufficiently brief as to be comparable with a regular teat dipping procedure and may be on the order of one to fifteen seconds. As supply 48 is used during dipping, the supply 48 may be replenished from the vessel supply 46, as above.

While shown using a plug 42 for connection via an extension cord or the like to conventional electrical supply, the teat dip 10 could advantageously be battery operated for ease of use, or include a rechargeable battery structure with the plug 42 being provided for recharging the batteries, as will be apparent to those skilled in the art.

Thus, the invention comprehends the use of ultrasound technology for sonically vibrating a germicide at ultrasonic frequencies during performance of a pre-milking or post-milking teat dipping operation.

We claim:

1. An ultrasound portable teat dip comprising:
   a dip cup of a size to be hand held by a user and having a well adapted to receive a supply of a germicide and an upper opening for receiving a teat to be dipped in the germicide, in use;
   a sonic transducer operatively coupled to the well to sonically vibrate the well to produce cavitation in the germicide supply;
   a storage vessel defining a reservoir for storing a supply of germicide;
   means for operatively securing said storage vessel to said dip cup;
   means for transferring germicide stored in said reservoir to said well to refill said dip cup with germicide; and
   means for connecting said sonic transducer to an electrical supply to drive said transducer.

2. The teat dip of claim 1 wherein said transducer comprises an ultrasonic transducer operatively coupled to the well to vibrate the well at an ultrasonic frequency.

3. An ultrasound teat dip comprising:
   a dip cup having a well adapted to receive a supply of a germicide and an upper opening for receiving a teat to be dipped in the germicide, in use;
   a sonic transducer operatively coupled to the well to sonically vibrate the well to produce cavitation on the germicide supply;
   a storage vessel defining a reservoir for storing a supply of germicide;
   means for operatively securing said storage vessel to said dip cup;
   means for transferring germicide stored in said reservoir to said well to refill said dip cup with germicide; and
   means for connecting said sonic transducer to an electrical supply to drive said transducer.

4. The teat dip of claim 3 wherein said transducer comprises an ultrasonic transducer operatively coupled to the well to vibrate the well.

5. The teat dip of claim 3 wherein said storage vessel comprises a jar having a top defining an upper opening and said securing means comprises a cap integrally formed with said dip cup for receiving the jar top.

6. The teat dip of claim 3 wherein said transferring means comprises a tube extending between said reservoir and said well.

7. The teat dip of claim 6 wherein said reservoir is formed of a pliable material which can be squeezed to force germicide through the tube to the well.

8. The method of performing a pre-milking or post-milking teat dip operation comprising the steps of:
   filling a dip cup having an upper opening with a supply of germicide, the dip cup being of a size adapted to be hand held by a user;
   sonically vibrating the dip cup to transmit sound waves through the germicide supply contained therein; and
   positioning the dip cup in proximity to a cow's udder to receive a teat in the germicide supply for a select period of time.

9. The method of claim 8 wherein said vibrating step comprises vibrating the dip cup at an ultrasonic frequency.

10. The method of claim 8 wherein said filling step comprises filling the dip cup from a storage vessel secured to said dip cup.

11. The method of claim 8 wherein said positioning step comprises maintaining the teat dipped in the germicide for a time period in the range of 1 to 15 seconds.

* * * * *